(12) United States Patent
Lesniak et al.

(10) Patent No.: US 7,775,214 B1
(45) Date of Patent: Aug. 17, 2010

(54) SPORTING PROPHYLAXIS

(75) Inventors: Frank Lesniak, Lansdale, PA (US); Naushirwan R. Mehta, Wellesley, MA (US); Gerard Kugel, Lexington, MA (US); Ayman Aboushala, Malden, MA (US)

(73) Assignee: Medtech Products, Inc., Irvington, NY (US)

( * ) Notice: Subject to any disclaimer, the term of this patent is extended or adjusted under 35 U.S.C. 154(b) by 0 days.

(21) Appl. No.: 11/741,557

(22) Filed: Apr. 27, 2007

(51) Int. Cl.
*A61F 5/37* (2006.01)
*A61F 13/00* (2006.01)
*A61F 5/56* (2006.01)
*A61C 5/14* (2006.01)
*A61C 3/00* (2006.01)

(52) U.S. Cl. ............... 128/861; 128/846; 128/848; 128/862; 433/6

(58) Field of Classification Search ............ 433/6, 433/37, 79–80, 168.1; 128/846, 848, 861–862
See application file for complete search history.

(56) References Cited

U.S. PATENT DOCUMENTS

| | | |
|---|---|---|
| 3,247,844 A | 4/1966 | Berghash |
| 3,496,936 A | 2/1970 | Gores |
| 3,505,995 A | 4/1970 | Greenberg |
| 4,063,552 A | 12/1977 | Going et al. |
| 4,668,188 A | 5/1987 | Wolfenson et al. |
| 4,761,136 A | 8/1988 | Madhavan et al. |
| 4,955,393 A | 9/1990 | Adell |
| 5,328,362 A * | 7/1994 | Watson et al. ............ 433/6 |
| 5,339,832 A | 8/1994 | Kittelsen et al. |
| 5,406,963 A | 4/1995 | Adell |
| 5,566,684 A | 10/1996 | Wagner |
| 5,624,257 A * | 4/1997 | Farrell ............ 433/6 |
| 5,646,216 A | 7/1997 | Watson et al. |
| 5,692,894 A * | 12/1997 | Schwartz et al. ............ 433/6 |
| 5,746,221 A | 5/1998 | Jones et al. |
| 5,755,233 A | 5/1998 | Adell |
| 6,036,487 A | 3/2000 | Westerman |
| 6,082,363 A | 7/2000 | Washburn |
| 6,170,485 B1 | 1/2001 | Orrico |
| 6,302,686 B1 | 10/2001 | Chott et al. |
| 6,935,857 B1 | 8/2005 | Farrell |
| 2006/0219250 A1 | 10/2006 | Farrell |

* cited by examiner

*Primary Examiner*—Patricia M Bianco
*Assistant Examiner*—Brandon Jackson
(74) *Attorney, Agent, or Firm*—Baker Donelson Bearman Caldwell & Berkowitz PC (57) ABSTRACT

An interocclusal sports prophylaxis includes a core having an arch shaped occlusal plate with upwardly extending buccal and lingual walls. A labial force dispersal shield and molar framing braces extend downwardly from the plate at incisor and lingual zones of the plate. The occlusal plate is thickened at the molar and incisor zones so that breathing spaces are provided between mandibular occlusal surfaces not registered with the zones and a mandibular face of the plate. A shock absorption dentition encasement is molded over the upper surface of the core and also covers the molar and incisor zones. The prophylaxis is heated in water, seated in the mouth and then biting pressure is applied to embed the maxillary dentition in the encasement and the lower incisor and molar occlusal surfaces in the encasement covering the zones.

22 Claims, 3 Drawing Sheets

SPORTING PROPHYLAXIS

BACKGROUND OF THE INVENTION

1. Field of the Invention

This invention relates generally to sporting equipment and more particularly to an interocclusal sports prophylaxis which protects both the upper and lower dentitions, as well as the temporomandibular joint, against impact.

2. Antecedents of the Invention

The earliest mouthguards were introduced in the 1920's for use in boxing and were formed of pieces of rubber cut to the shape of the maxillary arch and held in place by clenching the teeth together. It was difficult, if not impossible to achieve oral airflow because the teeth were required to be clenched together to maintain the mouthguard in position. Oral airflow was crucial, however, as increased levels of oxygen intake were required during physical exertion.

Additionally, early mouthguards were loose fitting and easily displaced upon impact. There was a significant risk of dislodgement and airway obstruction, which was particularly hazardous with reference to boxing, where there was a likelihood of a participant being rendered unconscious.

Improvements over the early rubber mouthguards included a design illustrated in U.S. Pat. No. 2,521,039, issued to Cartheter, which disclosed a rubber mouthguard having a central air passageway. Unfortunately, such mouthguard, too, was kept in place only by clenching and interfered with speech.

Attempts at improving rubber mouthguards lead to the employment of materials capable of conforming to tooth surfaces, including self fitted mouthguards which were immersed in boiling water and then formed in the mouth by biting. Problems encountered with such mouthguards included difficulty in centering the dentition during the self-fitting procedure.

In U.S. Pat. No. 5,566,684, issued to Wagner and assigned to the assignee of the present invention, there is disclosed a molded mouthguard having a thermoplastic channel shaped trough which carried a low softening temperature thermoplastic fill. After heating in boiling water, the mouthguard was inserted into the mouth and the fill conformed to the impression of the upper teeth when biting pressure was applied. Lacking, however, was positive engagement with the mandibular dentition.

In U.S. Pat. No. 5,406,963 issued to Adell, there was provided a mouthguard including a moldable liner which extended into both the upper end lower occlusal surfaces, however, such mouthguard lack the ability to adequately protect the lower dentition against shocks and further inhibited oral breathing, since there was intimate contact of both upper and lower occlusal surfaces with the liner material within which the occlusal surfaces were imbedded.

SUMMARY OF THE INVENTION

The present invention meets the need in the art by providing an interocusal sports prophylaxis comprising a single arch shaped occlusal plate that defines an upper mandibular face for abuttingly receiving occlusal maxillary surfaces and an opposing lower mandibular face for abuttingly receiving occlusal mandibular surfaces and at least two selected zones of the occlusal plate that have passageways therethrough, a dentition encasement material covering the selected zones and extending through the passageways, the dentition encasement material conforming to the shape of the respective mandibular and maxillary tooth surfaces after the prophylaxis is fitted and when the prophylaxis is worn, whereby when the prophylaxis is worn the opposing respective mandibular and maxillary tooth surfaces aligned with the passageways in the selected zones bear against detention encasement material extending through the passageways of the occlusal plate and the dentention encasement material resisting relative lateral and longitudinal movement of the mandibular and maxillary jaws.

Objects, features, and advantages of the present invention will become apparent upon a reading of the detailed description in conjunction with the drawings and the appended claims.

BRIEF DESCRIPTION OF THE DRAWINGS

In the accompanying drawings in which is shown some of the various exemplary embodiments of the invention.

DESCRIPTION OF THE PREFERRED EMBODIMENTS

Referring now in detail to the drawings, the reference numeral 10 denotes generally an interocclusal sports prophylaxis constructed in accordance with and embodying the invention. The prophylaxis 10 includes a lattice core 12 having a substantially planar dental arch shaped occlusal plate 14. The periphery of the upper or maxillary face of the plate is bordered by a buccal side wall 16 and a lingual side wall 18.

The occlusal plate 14 includes a pair of vertical molar passageways 20 and an incisor passageway 22 which extend between the maxillary face of the plate 14 and a lower or mandibular face 15.

Molded over the upper surfaces of the lattice core 12, i.e. the maxillary face of the plate 14 and the internal faces of the side walls 16, 18, is a shock absorption dentition encasement 24 formed or an EVA copolymer. A dental arch shaped channel 26 is formed on the upper surface of the encasement 24. The channel 26 serves as a guide for receiving the maxillary occlusal surfaces during a self fitting procedure, as will be explained in detail hereinafter. The EVA copolymer material of which the dentition encasement is formed extends through the passageways 20 and 22 such that an encasement layer 28 overlies a thickened molar zone or pedestal 30 which lies in a plane beneath the plane of the mandibular face 15. Similarly, the dentition encasement material extends through the incisor passageway 22 and an encasement layer 32 overlies a sloped thickened incisor zone 34 or pedestal which is positioned beneath the plane of the mandibular face 15.

As mentioned, the thickened molar zones or pedestals 30 include lower faces, each of which extends substantially parallel to the plane of the mandibular face 15. With the occlusal plate 14 having a thickness in the order of, for example, 1-2 mm, the thickness of the plate 14 at the molar zones would be in the order of 2-3 mm. That is, the plane of the face of the pedestals is approximately 1 mm below the plane of the mandibular face 15.

Figure 1:
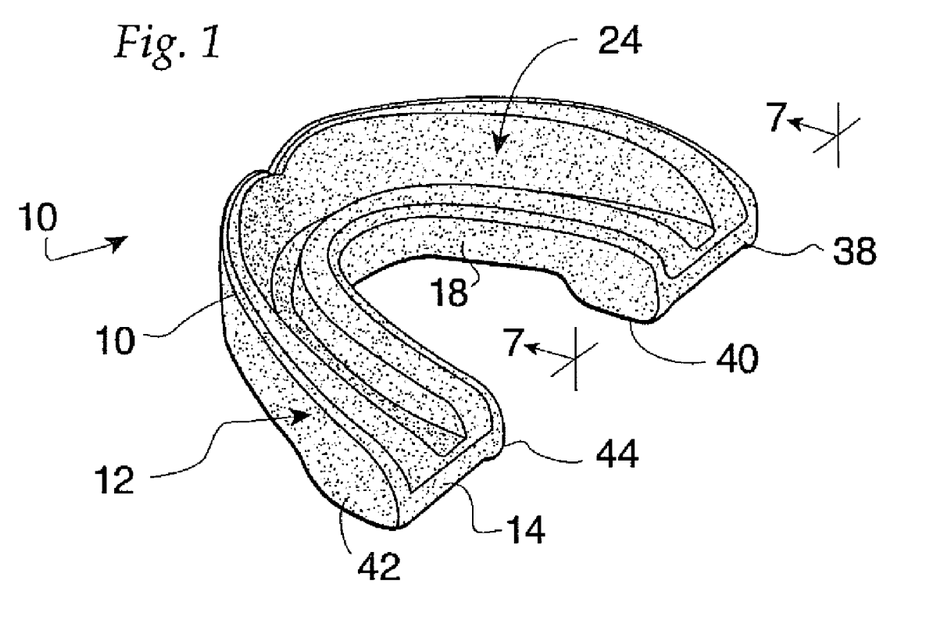
FIG. 1 is a perspective illustration of an interocclusal sports prophylaxis constructed in accordance with and embodying the invention and showing a core, the upper surface of which is covered by a dentition encasement material having a channel for receiving the maxillary dentition during a self fitting procedure.
Figure 2:
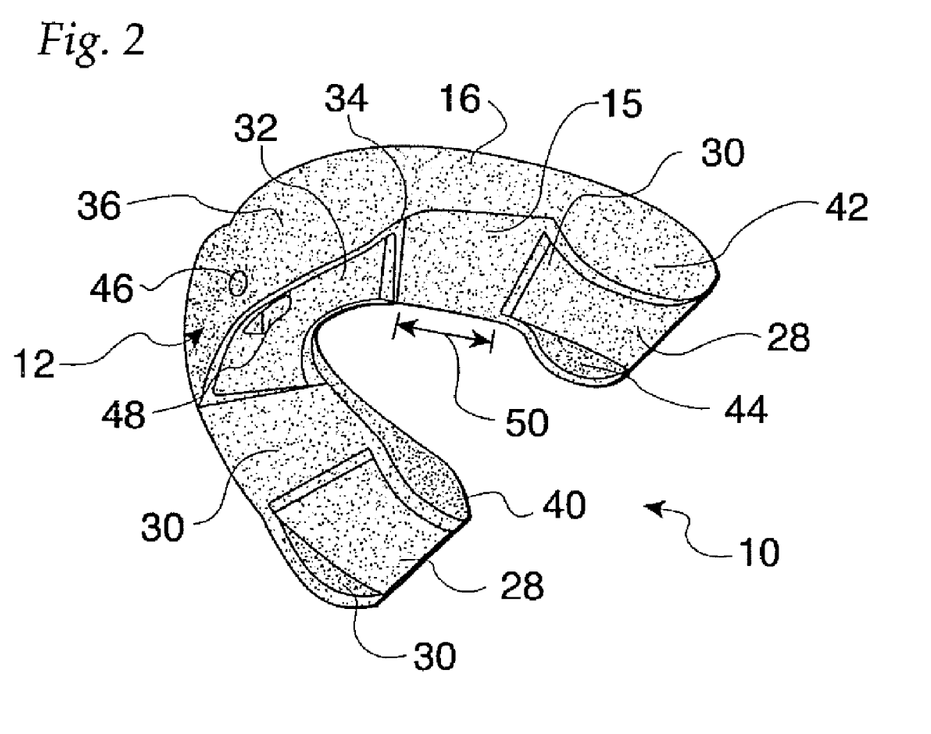
FIG. 2 is an underside perspective view of the interocclusal sports prophylaxis and showing a depending incisor force dispersal shield as well as a mandibular face of an occlusal plate of the core, with the face having thickened molar and incisor zones and with the core including framing braces at the molar zone.
Figure 3:
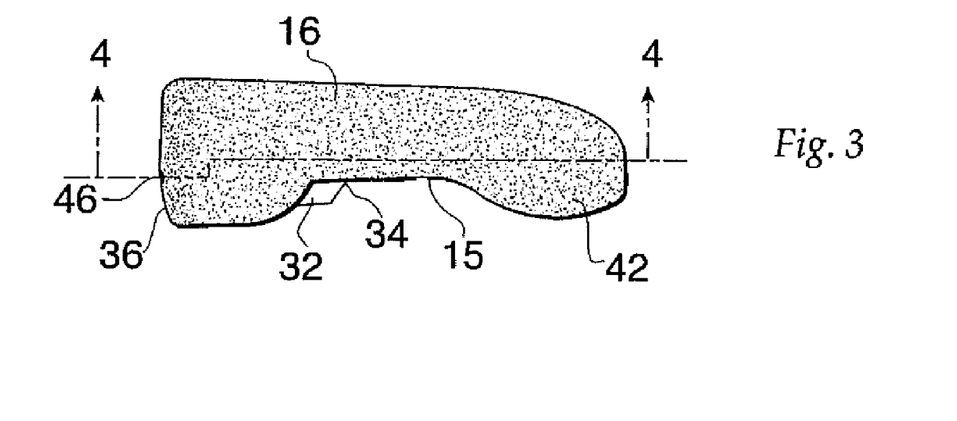
FIG. 3 is a left side view of the prophylaxis, illustrating the incisor force dispersal shield and a buccal molar framing brace.
Figure 4:
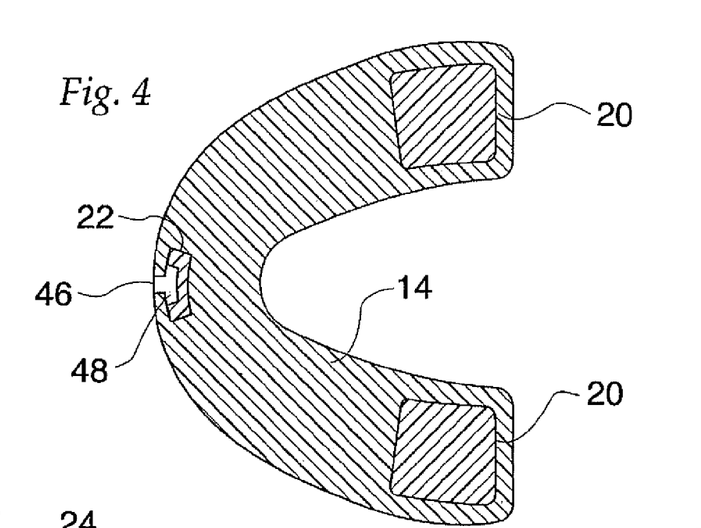
FIG. 4 is a sectional view through the occlusal plate, the same being taken substantially along the line 4-4 of FIG. 3 and illustrating dentition encasement material extending through passages in the plate.
Figure 5:
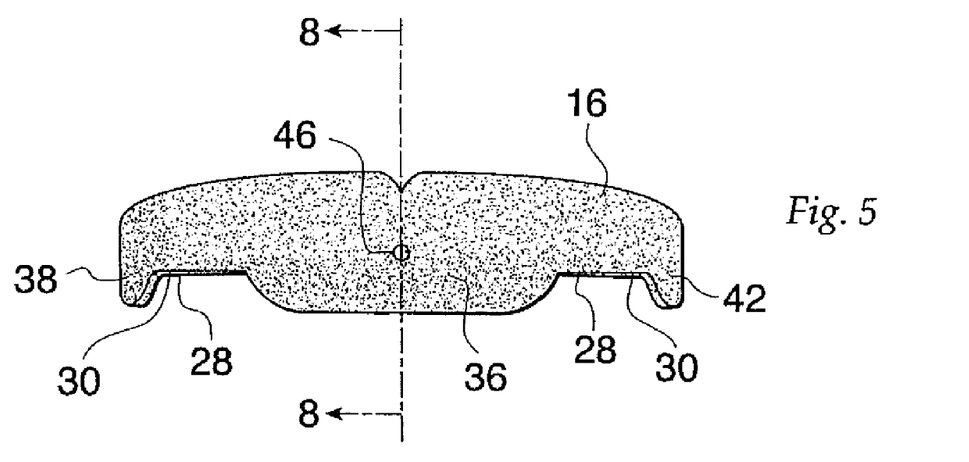
FIG. 5 is a front elevational view of the prophylaxis.
Figure 6:
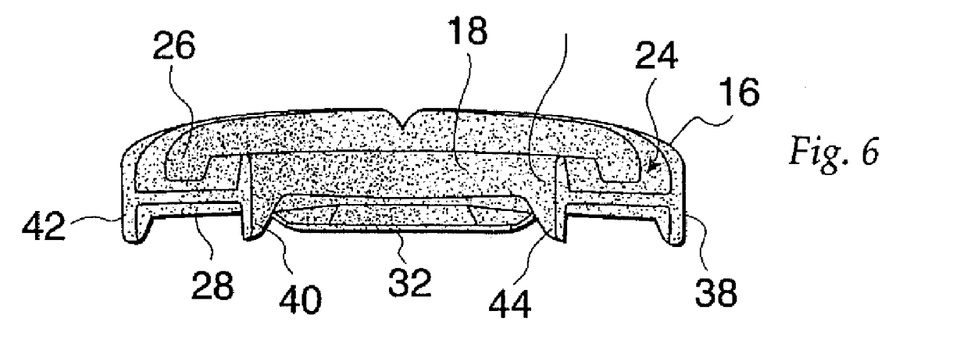
FIG. 6 is a rear elevational view thereof.
Figure 7:
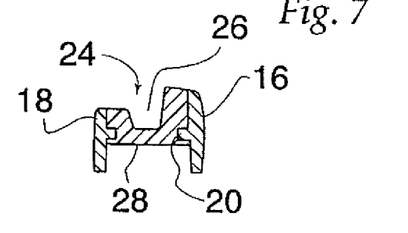
FIG. 7 is a sectional view through the right molar zone of the prophylaxis, the same being taken substantially along the plane 7-7 of FIG. 1.
Figure 8:
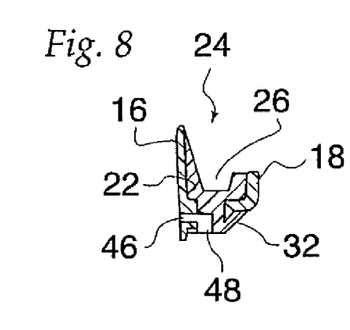
FIG. 8 is a sectional view through the incisor area of the prophylaxis, the same being taken substantially along the line 8-8 of FIG. 5.
Figure 9:
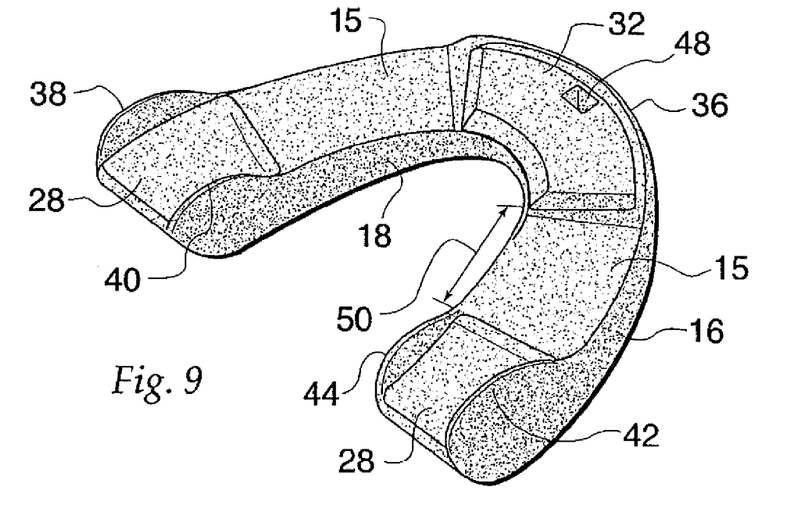
FIG. 9 is a further underside perspective view of the prophylaxis, similar to FIG. 2, however taken from the rear.

The thickness of the occlusal plate 14 at the incisor zone 34 is tapered or sloped from a maximum thickness at a labial force dispersal shield 36 (which is registered with an incisor area of the buccal wall 16) to a minimum thickness at a lingual bight as illustrated in FIG. 2 and FIG. 6. The thickness of the occlusal plate 14 at the incisor zone 34, at the point where contact with the mandibular incisors is expected to take place, is in the order of 3 to 5 mm, with the contact point lying in a plane approximately between 1 mm and 4 mm below the plane of the mandibular face 15.

Registered with the buccal wall 16 and the lingual wall 18 at the molar zones 30 are depending right molar framing braces 38, 40 and left molar framing braces 42, 44.

Pursuant to the invention, the right and left molar framing braces overly the buccal and lingual walls of the molars and thus serve to lock the mandible in place relative to the maxillary dentition in the presence of lateral blows which may be encountered during sporting events.

It should also be noted that a central aperture 46 extends through the force dispersal shield 36 and into a hollow companion well 48 molded in the incisor encasement layer 32 for the purpose of anchoring a tether strap which may be optionally utilized for attachment of the prophylaxis to a helmet component such as a cage or guard. A knot or enlarged end of the tether seats in the well 48.

The core 12 and the dentition encasement 24 are bonded to form a unitary prophylaxis which is fitted by immersion in hot water, such that the encasement material reaches a temperature above its softening temperature, yet which can be comfortably withstood by oral tissue. The prophylaxis is thereafter inserted into the oral cavity with the channel 26 substantially registered with the maxillary dentition.

Light pressure is applied to seat the maxillary dentition in the channel 26 after which biting pressure is applied to embed the maxillary teeth in the dentition encasement and to embed the molar and incisor occlusal surfaces of the mandibular dentition in the molar and incisor layers, 28, 32 which overlie the respective molar and incisor zones. The biting pressure is sufficient to displace the dentition encasement material such that the maxillary occlusal surfaces essentially abut the maxillary face of the occlusal plate 14 and the occlusal incisor and molar surfaces of the mandibular dentition abut the respective thickened molar and incisor zones 30, 34, formed on the mandibular face 15.

It should be appreciated that a mouth breathing air gap exists between the mandibular face 15 of the occlusal plate 14 and the lower cuspids, first bicuspids, second bicuspids and possibly first molars, when while the occlusal surfaces of the central and lateral incisors and second and third molars are embedded in the layers of encasement material which cover the respective thickened zones 30, 34.

There is a minimum distance 50 between each molar zone 30 and the incisor zone 34 in the order of 1.5 cm. With the thickness of the occlusal plate 14 at molar zones being in the order of 1 mm greater than the normal thickness of the occlusal plate 14 and the average thickness of the incisor zone 34 being in the order of 2 mm greater than the normal thickness of the occlusal plate 14, there is provided a minimum left and right free air breathing space between the mandibular occlusal surfaces and the mandibular face 15 of at least 15 sq. mm on both the left and the right sides, which results in a minimum total free air breathing space of at least 30 sq. mm.

It is significant that the thermoplastic material selected for the core has a softening temperature sufficiently above that of the dental encasement material such that the occlusal plate thickness at the molar zones and the incisor zone is not significantly reduced as a result of the compressor forces generated during the fitting procedure.

The rheological characteristics of the thermoplastic material from which the core 12 is fabricated include a Vicat softening temperature (ASTM D1525) of at least 65° C., which is well above the temperatures encountered during the fitting procedure, e.g. 40° C. to 45° C.

In accordance with the invention, the lattice core 12 is formed by injection molding of a thermoplastic resin have requisite characteristics into a mold cavity. The lattice core 12 is then positioned in a prophylaxis mold cavity and a thermoplastic resin material having the requisite characteristics for the dentition encasement is injected into the prophylaxis mold cavity over the core 12 and unitarily bonds thereto.

Suitable resins for employment as the dentition encasement material include an ethylene vinyl acetate (EVA) copolymer available from DuPont under the trademark ELVAX® having a vinyl acetate content of at least 25%. A preferred EVA copolymer is ELVAX® 150 having a 33% vinyl acetate content by weight, a Vicat softening temperature of 36° C. and a Shore A hardness of 73.

Preferred embodiments of the invention may be fabricated in accordance with the following examples:

EXAMPLE NO. 1

A lattice core 12 was injection molded utilizing the following resin formulation:

| CORE RESIN | PERCENTAGE BY WEIGHT |
| --- | --- |
| PELLETHANE ® 2103-90 A TPU elastomer | 90% |
| ELVAX ® 750 EVA | 10% |

PELLETHANE® 2103-90 A comprises a thermoplastic polyurethane elastomer available from Dow Chemical Co. and ELVAX® 750 EVA comprises an ethylene vinyl acetate copolymer available from DuPont and having a 9% vinyl acetate content by weight.

Ninety percent by weight PELLETHANE® 2103-90 A was blended with 10% ELVAX® 750 EVA by conventional apparatus such as a twin screw extruder, then pelletized. The blended pellets were then heated to a suitable molding temperature and thereafter molded into the lattice core mold cavity. The molded lattice core 12 exhibited a Shore A hardness of 90±1 and a Vicat softening temperature above 65° C.

The molded lattice core 12 was then inserted into a prophylaxis mold cavity and the following thermoplastic resin was utilized as the dentition encasement material:

| DENTITION ENCASEMENT RESIN | PERCENTAGE BY WEIGHT |
| --- | --- |
| ELVAX ® 150 EVA | 100% |

The ELVAX® 150 EVA encasement resin was heated to a suitable molding temperature and injection molded into a prophylaxis mold cavity, after the molded lattice core 12 had been positioned in the cavity.

The prophylaxis was removed from the mold cavity and exhibited a good adhesion between the lattice core and the dentition encasement.

The prophylaxis of EXAMPLE No. 1 was heated by immersion in boiling water for approximately 40 seconds, removed from the boiling water and immersed in water at or below room temperature for approximately 1 second. The prophylaxis was then inserted into the oral cavity and the maxillary occlusal surfaces were seated in the channel 26. Thereafter biting pressure was applied and the maxillary teeth were impressed into the dentition encasement. The encasement material flowed over, around and conformed to the shape of the surfaces of the maxillary dentition.

Simultaneously, the dentition encasement material in the molar layers 28 and the incisor layer 32 flowed over and around and conformed to the shape of the occlusal surfaces of the central and lateral incisors and second and third molars, leaving a free air gap between the remaining mandibular occlusal surfaces and the mandibular face 15. Both the maxillary and mandibular occlusal surfaces contacted the occlusal plate 14 of the core 12, having displaced the heated dentition encasement material. After fitting in the oral cavity in accordance with the invention, the free air gaps provided an adequate airway passage for mouth breathing, as would be required for increased oxygen intake during sporting activities.

EXAMPLE NO. 2

A lattice core 12 was injection molded utilizing the following resin formulation:

| CORE RESIN | PERCENTAGE BY WEIGHT |
| --- | --- |
| PELLETHANE ® 2103-90 A TPU elastomer | 90% |
| ELVALOY ® 1609 AC EMA | 10% |

Ninety percent by weight PELLETHANE® 2103-90 A was blended with 10% ELVALOY® 1609 AC ethylene methyl acrylate copolymer (available from DuPont) with conventional blending apparatus, by way of example, a twin screw extruder. The blended components were thereafter pelletized. The pellets were heated to a suitable molding temperature and injection molded into the lattice core mold cavity. The molded core exhibited a Shore A hardness of 90±1 and a Vicat softening temperature above 65° C.

The molded core 12 was then inserted into a prophylaxis mold cavity and the following resin was utilized as the dentition encasement material.

| DENTITION ENCASEMENT RESIN | PERCENTAGE BY WEIGHT |
| --- | --- |
| ELVAX ® 150 EVA | 100% |

The ELVAX® 150 EVA was heated to a recommended molding temperature above its melting point and injection molded into the prophylaxis mold cavity over the molded core 12.

The prophylaxis was removed from the mold cavity and exhibited a good adhesion bond between the dentition encasement and the lattice core.

The prophylaxis of EXAMPLE No. 2 was heated by immersion in boiling water for approximately 40 seconds, removed from the boiling water and immersed in water at or below room temperature for approximately 1 second. The prophylaxis was then inserted into the oral cavity and the maxillary occlusal surfaces were seated in the channel 26. Thereafter, biting pressure was applied and the maxillary teeth were impressed into the dentition encasement. The encasement material flowed over, around and conformed to the shape of the surfaces of the maxillary dentition.

Simultaneously, the dentition encasement material in the molar layers 28 and the incisor layer 32 flowed over and around and conformed to the shape of the occlusal surfaces of the central and lateral incisors and second and third molars, leaving a free air gap between the remaining mandibular occlusal surfaces and the mandibular face 15. Both the maxillary and mandibular occlusal surfaces contacted the occlusal plate 14 of the core 12, having displaced the heated dentition encasement material. After fitting in the oral cavity in accordance with the invention, the free air gaps provided an adequate airway passage for mouth breathing, as would be required for increased oxygen intake during sporting activities.

EXAMPLE NO. 3

A base 12 was injection molded utilizing the following resin formulation:

| CORE RESIN | PERCENTAGE BY WEIGHT |
| --- | --- |
| ELVALOY ® 1609 AC EMA | 100% |

ELVALOY® 1609 AC EMA was heated to a suitable molding temperature and thereafter injection molded into the core mold cavity. The molded core 12 exhibited a Shore A hardness of 90 and a Vicat softening temperature of 70° C. is specified by the manufacturer.

The molded core 12 was then inserted into an interocclusal sports prophylaxis mold cavity and the following thermoplastic resin was utilized as the impression preform:

| DENTITION ENCASEMENT RESIN | PERCENTAGE BY WEIGHT |
| --- | --- |
| ELVAX ® 150 EVA | 100% |

The ELVAX® 150 EVA was heated to a recommended molding temperature above its melting point and injection molded into the interocclusal sports prophylaxis mold cavity over the molded core.

The prophylaxis was removed from the mold cavity and exhibited a good adhesion between the lattice core and the dentition encasement.

The prophylaxis of EXAMPLE No. 3 was heated by immersion in boiling water for approximately 40 seconds, removed from the boiling water and immersed in water at or below room temperature for approximately 1 second. The prophylaxis was then inserted into the oral cavity and the maxillary occlusal surfaces were seated in the channel 26. Thereafter, biting pressure was applied and the maxillary teeth were impressed into the dentition encasement. The encasement material flowed over, around and conformed to the shape of the surfaces of the maxillary dentition.

Simultaneously, the dentition encasement material in the molar layers 28 and the incisor layer 32 flowed over and around and conformed to the shape of the occlusal surfaces of the central and lateral incisors and second and third molars, leaving a free air gap between the remaining mandibular occlusal surfaces and the mandibular face 15. Both the maxillary and mandibular occlusal surfaces contacted the occlusal plate 14 of the core 12, having displaced the heated dentition encasement material. After fitting in the oral cavity in accordance with the invention, the free air gaps provided an adequate airway passage for mouth breathing, as would be required for increased oxygen intake during sporting activities.

EXAMPLE NO. 4

A core 12 was injection molded utilizing the following resin formulation:

| CORE RESIN | PERCENTAGE BY WEIGHT |
|---|---|
| ELVAX ® 750 EVA | 100% |

ELVAX® 750 EVA was heated to a suitable molding temperature and thereafter injection molded into the core mold cavity. The molded base 12 exhibited a Shore A hardness of 92 and a Vicat softening temperature of 75° C. is specified by the manufacturer.

The prophylaxis was removed from the mold cavity and exhibited a good adhesion between the lattice core and the dentition encasement.

The prophylaxis of EXAMPLE No. 4 was heated by immersion in boiling water for approximately 40 seconds, removed from the boiling water and immersed in water at or below room temperature for approximately 1 second. The prophylaxis was then inserted into the oral cavity and the maxillary occlusal surfaces were seated in the channel 26. Thereafter, biting pressure was applied and the maxillary teeth were impressed into the dentition encasement. The encasement material flowed over, around and conformed to the shape of the surfaces of the maxillary dentition.

Simultaneously, the dentition encasement material in the molar layers 28 and the incisor layer 32 flowed over and around and conformed to the shape of the occlusal surfaces of the central and lateral incisors and second and third molars, leaving a free air gap between the remaining mandibular occlusal surfaces and the mandibular face 15. Both the maxillary and mandibular occlusal surfaces contacted the occlusal plate 14 of the core 12, having displaced the heated dentition encasement material. After fitting in the oral cavity in accordance with the invention, the free air gaps provided an adequate airway passage for mouth breathing, as would be required for increased oxygen intake during sporting activities.

EXAMPLE NO. 5

A core 12 was injection molded utilizing the following resin formulation:

| CORE RESIN | PERCENTAGE BY WEIGHT |
|---|---|
| ELVALOY ® 1609 AC EMA | 50% |
| PELLETHANE ® 2103-90 A TPU | 50% |

Fifty percent (50%) ELVALOY® 1609 AC by weight is blended with fifty percent (50%) PELLETHANE® 2103-90 A. The blend was heated to a suitable molding temperature and thereafter injection molded into the core mold cavity. Molded core 12 exhibited a Shore A hardness of 95 and a Vicat softening temperature above 65° C.

The molded core 12 was then inserted into an interocclusal sports prophylaxis mold cavity and the following thermoplastic resin was utilized as the encasement material:

| PREFORM RESIN | PERCENTAGE BY WEIGHT |
|---|---|
| ELVAX ® 150 EVA | 100% |

The prophylaxis was removed from the mold cavity and exhibited a good adhesion between the lattice core and the dentition encasement.

The prophylaxis of EXAMPLE No. 5 was heated by immersion in boiling water for approximately 40 seconds, removed from the boiling water and immersed in water at or below room temperature for approximately 1 second. The prophylaxis was then inserted into the oral cavity, with the maxillary occlusal surfaces were seated in the channel 26. Thereafter, biting pressure was applied and the maxillary teeth were impressed into the dentition encasement. The encasement material flowed over, around and conformed to the shape of the surfaces of the maxillary dentition.

Simultaneously, the dentition encasement material in the molar layers 28 and the incisor layer 32 flowed over and around and conformed to the shape of the occlusal surfaces of the central and lateral incisors and second and third molars, leaving a free air gap between the remaining mandibular occlusal surfaces and the mandibular face 15. Both the maxillary and mandibular occlusal surfaces contacted the occlusal plate 14 of the core 12, having displaced the heated dentition encasement material. After fitting in the oral cavity in accordance with the invention, the free air gaps provided an adequate airway passage for mouth breathing as would be required for increased oxygen intake during sporting activities.

Other suitable core resin formulations may comprise 100% ELVALOY® 1609 AC EMA, 100% ELVAX® 750 EVA, blends of ELVALOY® 1609 AC EMA and PELLETHANE®

2103-90 A TPU ranging between 10% to 90%, ELVALOY® 1609 AC EMA by weight, and blends of ELVAX® 750 EVA and PELLETHANE® 2103-90A TPU ranging between 90% to 10% ELVAX® 750 EVA by weight. Additional core resin formulations may comprise linear low density polyethylene (LLDPE), low density polyethylene (LDPE) or blends of ELVAX 750 EVA and LLDPE or LDPE with the LLDPE or LDPE content ranging from 25% to 90% by weight as well as 100% SANTOPRENE® 8000 Rubber (8281-90) having a Shore A hardness of 90.

It should be appreciated that the foregoing is merely exemplary and various other and alternate thermoplastic resins may be selected for use in accordance with the invention. The principal rheological and other attributes of the selected resins include a suitable softening temperature range for the encasement material resin which will not create temperature induced discomfort or damage to oral tissue, together with a softening temperature range and hardness of the core resin such that substantial deformation of the core does not occur during fitting and over prolonged usage.

Thus it will be seen that there is provided an interocclusal appliance which achieves the various aspects, features and considerations of the present invention and which is well-suited to meet the conditions of practical usage.

The apparatus and methods disclosed herein can be made and executed without undue experimentation in light of the present disclosure. While the apparatus of this invention have been described in terms of exemplary embodiments, it will be apparent to those of skill in the art that variations may be applied to the apparatus and in the method steps without departing from the concept, spirit and scope of the invention. All such similar substitutes and modifications apparent to those skilled in the art are deemed to be within the spirit, scope and concept of the invention as defined by the appended claims.

Having thus described the invention there is claimed as new and desired to be secured by Letters Patent:

1. An interoccusal sports prophylaxis comprising a single arch shaped occlusal plate that defines an upper mandibular face for abuttingly receiving occlusal maxillary surfaces and an opposing lower mandibular face for abuttingly receiving occlusal mandibular surfaces and at least two selected zones of the occlusal plate that have passageways therethrough, a dentition encasement material covering the selected zones and extending through the passageways, the dentition encasement material conforming to the shape of the respective mandibular and maxillary tooth surfaces after the prophylaxis is fitted and when the prophylaxis is worn, whereby when the prophylaxis is worn the opposing respective mandibular and maxillary tooth surfaces aligned with the passageways in the selected zones bear against detention encasement material extending through the passageways of the occlusal plate and the dentention encasement material resisting relative lateral and longitudinal movement of the mandibular and maxillary jaws.

2. The interocclusal sports prophylaxis as recited in claim 1 wherein the dentition encasement material is molded to the plate.

3. The interocclusal sports prophylaxis as recited in claim 1 wherein the mandibular face is generally planar except at the selected zones, the occlusal plate extending below the plane of the mandibular face at the selected zones.

4. The interocclusal sports prophylaxis as recited in claim 3 wherein the occlusal plate extends below the plane of the mandibular face a distance in the order of at least one mm at the selected zones.

5. The interocclusal sports prophylaxis as recited in claim 4 wherein one of the selected zones is an incisor zone and the occlusal plate extends below the plane of the mandibular face a distance in the order of two mm at the incisor zone.

6. The interocclusal sports prophylaxis as recited in claim 1 wherein the plate comprises a resin which includes a thermoplastic polyurethane elastomer.

7. The interocclusal sports prophylaxis as recited in claim 6 wherein the thermoplastic polyurethane elastomer is blended with a thermoplastic selected from the group consisting of ethylene vinyl acetate copolymer and ethylene methyl acrylate copolymer.

8. The interocclusal sports prophylaxis as recited in claim 6 wherein the resin comprises about 90% by weight thermoplastic polyurethane elastomer and about 10% by weight ethylene vinyl acetate copolymer.

9. The interocclusal sports prophylaxis recited in claim 6 wherein the resin comprises about 90% by weight thermoplastic polyurethane elastomer and about 10% by weight ethylene methyl acrylate copolymer.

10. The interocclusal sports prophylaxis as recited in claim 1 wherein the plate comprises a resin having a first hardness and a first softening temperature and the dentition encasement material comprises a resin having a second hardness and a second softening temperature, said second hardness less than the first hardness and the second softening temperature less than the first softening temperature.

11. The interocclusal sports prophylaxis as recited in claim 1 wherein the selected zones are a pair of molar zones and an incisor zone and the minimum distance between the molar zones and the incisor zone is in the order of 1.5 cm.

12. The interocclusal sports prophylaxis as recited in claim 1, wherein the dentition encasement material defines in the selected zones pedestals having mandibular surfaces in a plane spaced from a plane defined by the occlusal plate, whereby mandibular occlusal surfaces not registered with the selected zones are spaced from the opposing mandibular face to provide oral breathing passages between non-registered mandibular tooth surfaces and the mandibular face when the prophylaxis is worn.

13. An interocclusal sports prophylaxis comprising a single arch shaped occlusal plate that defines an upper mandibular face for abuttingly receiving occlusal maxillary surfaces and an opposing lower mandibular face for abuttingly receiving occlusal mandibular surfaces and at least two selected zones of the occlusal plate having passageways therethrough, a dentition encasement material covering within the selected zones and extending through the passageways, a labial force dispersal shield extending downwardly from a peripheral portion of the occlusal plate to protect a user's incisor mandibular structure against frontal blows during sporting activities, a pair of opposed peripheral framing braces, each framing brace extending downwardly from a buccal periphery of the mandibular face at a molar zone to protect the user's mandibular structure against lateral blows encountered during sporting activities, the buccal periphery of the mandibular face being free of downward extensions intermediate the labial force dispersal shield and the framing braces to facilitate oral breathing, and the dentition encasement material conforming to the shape of the respective mandibular and maxillary tooth surfaces after the prophylaxis is fitted and when the prophylaxis is worn, whereby when the prophylaxis is worn the opposing respective mandibular and maxillary tooth surfaces aligned with the passageways in the selected zones bear against detention encasement material extending through the passageways of the occlusal plate and and the encasement material resisting relative lateral and longitudinal movement of the mandibular and maxillary jaws.

14. The interocclusal sports prophylaxis as recited in claim 13, wherein the dentition encasement material defines in the selected zones pedestals having mandibular surfaces in a plane spaced from a plane defined by the occlusal plate, whereby mandibular occlusal surfaces not registered with the selected zones are spaced from the opposing respective upper and lower mandibular face to provide oral breathing passages between non-registered mandibular tooth surfaces and the respective upper and lower mandibular face when the prophylaxis is worn.

15. The interocclusal sports prophylaxis as recited in claim 13 wherein the dentition encasement material covers the molar zones in registration with mandibular molar teeth of the user and an incisor zone of the mandibular face, the incisor zone being registered with the labial force dispersal shield.

16. The interocclusal sports prophylaxis as recited in claim 13 wherein the mandibular face further includes an incisor zone, the incisor zone and the molar zones extending below a plane of the mandibular face, whereby mandibular occlusal surfaces of a user not registered with the incisor zone and the molar zones are spaced from the mandibular face to provide opposed oral breathing passages when the prophylaxis is worn.

17. An interocclusal sports prophylaxis comprising a single arch shaped occlusal plate that defines an upper mandibular face for abuttingly receiving occlusal maxillary surfaces and an opposing lower mandibular face for abuttingly receiving occlusal mandibular surfaces, and having breathing passage zones across the occlusal plate intermediate a respective one of a pair of opposing molar zones and an incisor zone, the occlusal plate having at least in the molar zones passageways therethrough, a dentition encasement material covering the molar zones and extending through the passageways, whereby when the prophylaxis is worn the opposing respective mandibular and maxillary tooth surfaces aligned with the passageways in the molar zones bearing against detention encasement material extending through the passageways of the occlusal plate, the dentition encasement material covering the molar zones and the incisor zones defining pedestals having mandibular surfaces in a plane spaced from a plane defined by manibular surfaces of the breathing passage zones, the dentition encasement material conforming to the shape of the respective mandibular and maxillary tooth surfaces after the prophylaxis is fitted and when the prophylaxis is worn, whereby mandibular occlusal surfaces registered with the breathing passage zones are spaced from the opposing mandibular face to provide oral breathing passages between mandibular tooth surfaces and the mandibular face when the prophylaxis is worn and the encasement material resisting relative lateral and longitudinal movement of the mandibular and maxillary jaws when the prophylaxis is worn.

18. The interocclusal sports prophylaxis as recited in claim 17 wherein the mandibular face is generally planar except at the molar and incisor zones, the occlusal plate extending below the plane of the mandibular face thereat.

19. The interocclusal sports prophylaxis as recited in claim 18 wherein the occlusal plate extends below the plane of the mandibular face a distance in the order of at least one mm.

20. The interocclusal sports prophylaxis as recited in claim 19 wherein the occlusal plate extends below the plane of the mandibular face a distance in the order of two mm at the incisor zone.

21. The interocclusal sports prophylaxis as recited in claim 17 wherein the plate comprises a resin having a first hardness and a first softening temperature and the dentition encasement material comprises a resin having a second hardness and a second softening temperature, said second hardness less than the first hardness and the second softening temperature less than the first softening temperature.

22. The interocclusal sports prophylaxis as recited in claim 17 wherein the breathing passages comprise not less than 30 sq. mm.

* * * * *

UNITED STATES PATENT AND TRADEMARK OFFICE
CERTIFICATE OF CORRECTION

| | | |
|---|---|---|
| PATENT NO. | : 7,775,214 B1 | Page 1 of 1 |
| APPLICATION NO. | : 11/741557 | |
| DATED | : August 17, 2010 | |
| INVENTOR(S) | : Frank Lesniak et al. | |

It is certified that error appears in the above-identified patent and that said Letters Patent is hereby corrected as shown below:

In column 10, line 67, after the word "plate" remove "and".

Signed and Sealed this
Eighth Day of March, 2011

David J. Kappos
*Director of the United States Patent and Trademark Office*